United States Patent
Marechal et al.

(10) Patent No.: US 7,569,236 B2
(45) Date of Patent: Aug. 4, 2009

(54) SUSTAINED-RELEASE MICROGRANULES CONTAINING GINGKO BILOBA EXTRACT AND THE PROCESS FOR MANUFACTURING THESE

(75) Inventors: Dominique Marechal, Laval (CA); Wei-hong Yang, Shanghai (CN); Yu-zhang Hu, Shanghai (CN)

(73) Assignee: Ethypharm, Houdan (FR)

( * ) Notice: Subject to any disclaimer, the term of this patent is extended or adjusted under 35 U.S.C. 154(b) by 54 days.

(21) Appl. No.: 10/574,923

(22) PCT Filed: Oct. 11, 2004

(86) PCT No.: PCT/IB2004/003542

§ 371 (c)(1),
(2), (4) Date: May 19, 2006

(87) PCT Pub. No.: WO2005/034923

PCT Pub. Date: Apr. 21, 2005

(65) Prior Publication Data

US 2007/0009598 A1   Jan. 11, 2007

(30) Foreign Application Priority Data

Oct. 10, 2003   (EP)   ................... 03292512

(51) Int. Cl.
*A61K 36/16* (2006.01)
*A61K 9/14* (2006.01)
*A61K 9/16* (2006.01)

(52) U.S. Cl. ................. 424/752; 424/489; 424/490; 424/493; 424/497; 424/498

(58) Field of Classification Search ............ 424/752, 424/489, 490
See application file for complete search history.

(56) References Cited

U.S. PATENT DOCUMENTS

| | | | |
|---|---|---|---|
| 4,411,882 A | 10/1983 | Franz | |
| 4,960,596 A | 10/1990 | Debregeas et al. | |
| 5,026,560 A | 6/1991 | Makino et al. | |
| 5,104,661 A | 4/1992 | Lau et al. | |
| 5,384,130 A | 1/1995 | Kamada | |
| 5,385,739 A | 1/1995 | Debregeas et al. | |
| 5,427,800 A | 6/1995 | Cingotti et al. | |
| 5,733,551 A | 3/1998 | Jacob et al. | |
| RE35,903 E | 9/1998 | Debregeas et al. | |
| 5,876,758 A | 3/1999 | Meybeck et al. | |
| 5,965,165 A | 10/1999 | Zannini et al. | |
| 6,030,621 A | 2/2000 | De Long et al. | |
| 6,056,949 A | 5/2000 | Menzi et al. | |
| 6,077,544 A | 6/2000 | Debregeas et al. | |
| 6,120,802 A | 9/2000 | Breitenbach et al. | |
| 6,228,395 B1 | 5/2001 | Debregeas et al. | |
| 6,340,478 B1 | 1/2002 | Blatt et al. | |
| 6,383,516 B1 | 5/2002 | Debregeas et al. | |
| 6,391,342 B1 * | 5/2002 | Henriksen et al. | 424/490 |
| 6,458,389 B1 | 10/2002 | Debregeas et al. | |
| 6,482,437 B2 | 11/2002 | Debregeas et al. | |
| 6,551,621 B1 | 4/2003 | Debregeas et al. | |
| 6,660,296 B2 | 12/2003 | Debregeas et al. | |
| 6,770,298 B1 | 8/2004 | Debregeas et al. | |
| 6,962,717 B1 * | 11/2005 | Huber et al. | 424/490 |
| 2004/0081691 A1 * | 4/2004 | Debregeas et al. | 424/465 |
| 2005/0058704 A1 * | 3/2005 | Schneider et al. | 424/458 |
| 2006/0204576 A1 * | 9/2006 | Petereit et al. | 424/472 |
| 2006/0280789 A1 * | 12/2006 | Ueki et al. | 424/464 |

FOREIGN PATENT DOCUMENTS

| | | | |
|---|---|---|---|
| CN | 1371744 A | * | 10/2002 |
| DE | 24 58 112 | | 2/1976 |
| EP | 0 290 299 | | 11/1988 |
| EP | 0 687 466 | | 12/1995 |
| FR | 1443063 | | 5/1966 |
| FR | 2616068 | | 12/1988 |
| WO | WO-93/12761 | | 7/1993 |
| WO | WO-98/16111 | | 4/1998 |
| WO | WO 00/69414 A2 | | 11/2000 |

OTHER PUBLICATIONS

O'Hara et al., "A Review of 12 Commonly Used Medicinal Herbs," Nov. 1998, Archives of Family Medicine, vol. 7, No. 6, pp. 523-536.*
International Preliminary Examination Report for PCT/FR00/01316 dated Jul. 17, 2000.
International Search Report for PCT/FR00/01316; dated May 17, 2000.
Office Action issued Aug. 20, 2008, in U.S. Appl. No. 10/689,469, 9 pages.
Office Action issued Mar. 8, 2007, in U.S. Appl. No. 10/689,469, 11 pages.
Office Action issued Nov. 3, 2006, in U.S. Appl. No. 10/689,469, 5 pages.
Office Action issued Sep. 21, 2007, in U.S. Appl. No. 10/689,469, 10 pages.
Webster's Dictionary, p. 331, 792 (Riverside Publishing, 1992).
Nissenson et al.; "Mannitol"; The Western Journal of Medicine; 1979, vol. 131, pp. 277-284.
Handbook of Pharmaceutical Excipients (2000) on PVP, "Povidone", pp. 508-509.

* cited by examiner

*Primary Examiner*—Christopher R. Tate
(74) *Attorney, Agent, or Firm*—Foley & Lardner LLP

(57) ABSTRACT

The subject of the present invention is a new stable herbal drug formulation in the form of sustained-release microgranules containing *Gingko Biloba* extract as well as the process for preparing it.

27 Claims, No Drawings

SUSTAINED-RELEASE MICROGRANULES CONTAINING GINGKO BILOBA EXTRACT AND THE PROCESS FOR MANUFACTURING THESE

This application is a National Stage application of PCT/IB2004/003542, filed Oct. 11, 2004, which claims priority from European patent application EP 03292512.5, filed Oct. 10, 2003. The entire contents of each of the aforementioned applications are incorporated herein by reference.

The subject of the present invention is a new stable formulation in the form of sustained-release microgranules containing *Ginkgo biloba* extract as well as the process for preparing it.

More precisely, the present invention relates to microgranules in the form of a core containing *Ginkgo biloba* extract with at least one pharmaceutically acceptable excipient, an intermediate layer coating said core, and an outer layer, which enables sustained release of *Ginkgo biloba* from the core.

*Ginkgo biloba* extract contains flavone glycosides (flavonoids), such as quercetin, kaemferol, isorhamnetin and terpenes (heterosides) such as Bilobadide, ginkgolide A, ginkgolide B, ginkgolide C, ginkgolide J.

Flavonoids are known to have anti Platelet-activiting Factor properties, thus terpenes have corticoid-like, anti-ischaemic properties and are known to be antagonists of peripherical benzodiapine receptors, inducing anti-stress activity.

Powders extracted from plant substances are usually very hygroscopic and they therefore pump moisture from the granules and from the gelatin capsule, which become brittle. This leads to poor stability properties.

Plant extracts have poor flowability and compressibility properties. Thus, formulation of such extracts in the form of sustained release tablets is not possible, as it requires homogeneous mixtures of extracts with pharmaceutical excipients during all compression steps.

WO 00/69414 relates to granules containing at least one plant substance, characterized in that they each comprise a neutral core, which has a grain size of between 200 and 4000 µm and which is coated with a layer containing the plants substance, combined with a pharmaceutically suitable excipient.

The multiparticulate form of the invention makes it possible to obtain a stable and reproducible sustained release multiparticulate dosage form comprising *Ginkgo biloba* extract, with the advantage of being stable during storage, particularly in accelerated storage conditions, defined in ICH as 40° C. for temperature and 75% for relative humidity.

According to the present invention, the sustained release microgranules contain a *Ginkgo biloba* extract, characterized by the release of total flavone glycosides having the following profile of dissolution rates, measured at 37.0° C.±0.5° C., with a Dissolution Test Apparatus I (Basket method at 100 rpm, 900 mL of purified water, W Detection 272 nm):

| T (h)    | DISSOLUTION (w/w) |
|----------|-------------------|
| 0.5 hour | ≦45%              |
| 2 hours  | <75%              |
| 8 hours  | >60%              |

More specifically, the sustained release microganules are characterized by the following profile:

| T (h)    | Dissolution (w/w) |
|----------|-------------------|
| 0.5 hour | 5-45%             |
| 2 hours  | 30-70%            |
| 8 hours  | >60%              |

These granules containing *Ginkgo biloba* extract are further characterized in that they comprise:
- a neutral core coated with a layer containing *Ginkgo biloba* extract, with at least one pharmaceutically acceptable excipient,
- an optionnal water-repellent layer, coating said core, comprising at least a polymer or a thermoplastic excipient,
- an outer polymeric layer which sustain the release of said extract from the active core.

*Ginkgo biloba* extract may be in a concentrated preparation which are liquid, solid or of intermediate consistency, generally obtained from dried plant raw materials, preferably leaves, or in a powder form.

Fluid extracts are liquid preparations of which, in general, a portion by mass or by volume corresponds to a portion by mass of dried raw material. These preparations are adjusted, if necessary, so as to meet the requirements of content of solvents, of constituents or of dry residue.

Soft extracts are preparations having an intermediate consistency between fluid extracts and dry extracts. Soft extracts are prepared by partial evaporation of the solvent which served for their preparation. Only ethanol at an appropriate title or water is used. Soft extracts have in general a dry residue which is not less than 70 per cent by weight. They may contain appropriate antimicrobial preservatives.

Dry extracts are solid preparations obtained by evaporation of the solvent which served for their production. Dry extracts have in general a dry residue which is not less than 95 per cent by weight. Appropriate inert substances may be added.

The plant powders are obtained from whole plants or fragmented or cut plant portions, used as they are, in desiccated form.

*Ginkgo biloba* extracts contain up to 40% by weight of flavonoids, and up 10% by weight of terpenes.

Preferred *Ginkgo biloba* extracts contain 24% by weight of flavonoids and 6% by weight of terpenes.

The neutral core consists of a substance chosen from sugar, starch, mannitol, sorbitol, xylitol, cellulose, talc and mixtures thereof.

The neutral core may also consist of a starch/sucrose core in 80/20 mass ratios which is coated with 80% by weight of starch. In such neutral cores, the proportion by mass of sugar is advantageously less than 20%.

The layer containing the *Ginkgo biloba* extract contains at least one pharmaceutically acceptable excipient, selected from the group comprising a binder, an antistatic agent or a lubricant, preferably a binder.

The binder is selected from the group consisting of cellulosic polymers, such as ethylcellulose, hydroxypropylcellulose and hydroxypropylmethyl cellulose, acrylic polymers, such as insoluble acrylate ammoniomethacrylate copolymer, polyacrylate as polymethacrylic copolymer, povidones, copovidones, polyvinylalcohols, shellac, alginic acid, sodium alginate, starch, pregelatinized starch, sucrose and its derivatives, guar gum, polyethylene glycol, preferably polyvinylpyrrolidone (PVP) or shellac.

The binder is used in proportions of at most about 50%, preferably at most 20% by weight of *Ginkgo biloba* extract.

The antistatic agent, which can be used as flow aid, is selected from the group consisting of micronised or non micronised talc, fumed silica (Aerosilâ R972), colloidal silica (Aerosil® 200), precipitated silica (Syloïd® FP244) and mixtures thereof.

The antistatic agent is used in proportions of at most 5%, preferably 2% by weight relative to the weight of said granules of GB extract.

The lubricant is selected from the group consisting of magnesium stearate, stearic acid, sodium stearyl fumarate, micronised polyoxyethyleneglycol (micronised Macrogol 6000), leukine, sodium benzoate and mixtures thereof.

The amount of lubricant is from 0 to 3%, preferably from 1 to 2% by weight, based on the weight of the granules.

In order to prevent sticking between granules, mainly due to Ginkgo biloba extract, it is necessary to optionally apply an intermediate layer between the active layer comprising the *Ginkgo biloba* extract and the polymeric layer ensuring sustained release of said extract.

Said intermediate water-repellent layer comprises at least a polymer or a thermoplastic excipient.

The polymer is selected from the group of binders, preferably PVP.

In the context of the present invention, thermoplastic excipient refers to compounds having a melting point of between 25 and 100° C. and characterized by a pasty to semi-solid consistency at temperature of about 20° C.

The thermoplastic excipient may be chosen from partially hydrogenated oils, beeswax, carnauba wax, paraffin waxes, silicone waxes, C12-C18 fatty alcohols and fatty acids, solid, semi-synthetic glycerides, glycerol monoesters, diesters or triesters, polyoxyethylene glycols and glycosylated polyoxyethylenated glycerides, preferably monostearate glyceride and mixtures thereof.

In order to ensure a sustained dissolution profile of the active substance the granules are coated with a coating composition containing at least one coating agent selected from the group consisting of cellulosic polymers, acrylic polymers, shellac and mixtures thereof.

Among cellulosic polymers, ethylcellulose, hydroxypropylcellulose and hydroxypropylmethylcellulose are advantageously used.

Among acrylic polymers, insoluble acrylate ammoniomethacrylate copolymer (Eudragit® RL100 or RS100 or Eudragit® RL30D or RS30D), polyacrylate (Eudragit®NE30D), or methacrylic copolymers (Eudragit® L100-55 or Eudragit® L30D, Eudragit® E100, Eudragit® EPO) are advantageously used, alone, in combination.

Optionally plasticizers, surfactants, antistatic agents or lubricants are added as coating additives.

The plasticizer is selected in the group consisting of dibutyl sebacate triacetine, triethylacetate, triethylcitrate, ethylphtalate, or mixtures thereof. The plasticizer is used in proportions of at most about 30%, preferably 10% by weight of the coating agents.

The surfactant may be an anionic, nonionic, cationic or amphoteric surfactant.

The antistatic agent is selected from the group comprising micronised or non micronised talc, fumed silica (Aerosil® R972), colloidal silica (Aerosil® 200), precipitated silica (Syloïd® FP244) and mixtures thereof.

The antistatic agent is used in proportions of at most about 10%, preferably between 0 and 3% by weight, more preferably less than 1% by weight.

The lubricant is selected in the group comprising magnesium stearate, stearic acid, sodium stearyl fumarate, micronized polyoxyethyleneglycol, sodium benzoate and mixtures thereof.

Determination of workable precise proportions in any particular instance will generally be within the capability of the man skilled in the art.

All indicated proportions and relative weight ranges described above are accordingly to be understood as being indicative of preferred or individually inventive teachings only and not as limiting the invention in its broadest aspect.

The present invention also relates to a process for the preparation of the granules described above.

The process according to the invention allows better reproducibility of the proportion.

Microgranules can be manufactured by a number of different processes, for example extrusion-spheronization, fluid air bed process or a coating-pan method.

Extrusion-Spheronization is suitable for pellets with high content of active substance, but need more equipment.

For the manufacture of the granules of the invention, the coating-pan method is preferred, as it requires only simple equipment and operation.

Good sphericity and appropriate size of microgranule benefit to control drug release by coating film and to achieve good stability of the finished product.

The process for the preparation of sustained-release microgranules containing *Ginkgo biloba* extract comprises the successive steps consisting in:

Applying over a neutral core, a layer comprising *Ginkgo biloba* extract, and at least one pharmaceutical excipient, preferably a binder.

Coating said core with an intermediate layer over the thus obtained granules by spraying thereon a suspension, or a solution comprising a polymer or a thermoplastic excipient Coating the thus coated granules with an outer layer by spraying a suspension, a dispersion or a solution of a sustained-release coating composition, Drying the thus obtained coated granules.

In this process, all steps can be performed in different or in the same equipment, each step being performed in the presence of a mixture of excipients which are identical or different.

The prepared coating liquid is either water-based or prepared using organic solvents, preferably isopropylic alcohol. According to an advantageous embodiment, this coating liquid is suitable to be sprayed with conventional spray layering equipment, as for example a coating pan or a fluidized air bed equipped with a top insert or bottom (würster) insert.

According to the process of the invention, the cores are obtained by powder-coating, advantageously carried out by alternately spraying an alcoholic or aqueous-alcoholic solution comprising at least one pharmaceutical excipient, preferably a binder, and the *Ginkgo biloba* extract.

The granules according to the invention are prepared according to coating techniques known in the art, preferably in a pan or in a fluidized air bed.

The invention is illustrated without any limitation by the following examples.

In the examples below, the following excipients are used:
*Ginkgo Biloba* extract containing 24% by weight of flavone glycosides and 6% by weight of terpene): Zhejiang Conba Pharmaceutical Co. Ltd.
Neutral cores: NP Pharm
PVP K30: Shanghai Huayi economy and trade industry of science and technology Co.Ltd.

Shellac: Alland & Robert
Talc Shanghai Tianpin pharmaceutical factory
Ethylcellulose: FMC
Monostearate glycerides
Dibutyl Sebacate Dissolution Test Method This method was developed in order to detect release of total flavone glycosides from microgranules containing *Ginkgo biloba* extract.

Apparatus: Dissolution Test Apparatus I (Basket method)
Speed: 100 rpm
Volume: 900 mL of purified water
Temperature: 37.0° C.±0.5° C.
Sampling (mL): 10 ml
UV Detection: UV at 272 nm Water Content Assay Water content is determined using Karl Fischer Water determination.

Content Assay Method

This method was developed in order to assay total flavone glycosides content from microgranules containing *Ginkgo biloba* extract, and specifically assay quercetin, kaemfortol and isohamnetin content from granules.

Source: Chinese Pharmacopeia 2000 Part One, Appendix VI D

Apparatus: HP 1100 Liquid Chromatograph (including quaternary pump, UV detector, diode array detector, chemical work station), Chromatographic conditions HPLC Column: $C_{18}$ 4,6*250 nm 15 μm Beijing Dima
Mobile Phase: methanol, 0,4% v/v phosphoric acid solution (50/50) Sampling: 10 μl UV Detection: 360 nm

EXAMPLE 1

Step 1—Drug Loading 84 grams of neutral cores are placed in a coating-pan, A 10% (w/w) binding solution of shellac, dissolved in isopropyl alcohol is prepared, then sprayed over neutral core as *Ginkgo biloba* extract is gradually added at the same time.

Granules are then sieved and dried for 10 hour at 60° C.

Step 2—Intermediate Water-repellent Coating 4,8 grams of monsterate glycerides are dissolved in isopropyl alcohol at 10% (w/w) and the resulting solution is sprayed over granules from step 1.

Step 3—Sustained-release Coating

The thus obtained granules were coated by spraying thereon a water dispersion of Aquacoat ECD30 at 16% (weight/weight) containing dibutyl sebacate as plasticizer (25% versus dry polymer).

The amount of coating was of 8% by weight with respect to the weight of the granules from step 2.

Coated microgranules are then sieved and dried in a coating pan at 65° C. for 10 hours.

The sustained-release microgranules resulting from the process have the following formula (table 1):

TABLE 1

| Name of ingredients | function | Unit formula (g) | Percentage formula (% w/w) |
|---|---|---|---|
| Ginkgo extract | Active substance | 120.0 | 50.0 |
| Neutral granules | Cores | 84.0 | 35.0 |

TABLE 1-continued

| Name of ingredients | function | Unit formula (g) | Percentage formula (% w/w) |
|---|---|---|---|
| Shellac | Binding agent | 9.6 | 4.0 |
| Aquacoat ECD30 | Coating agent | 16.8 | 7.0 |
| Dibutyl sebacate | Plasticiser | 4.1 | 1.7 |
| Monstearate glyceride | Water-repellent agent | 4.8 | 2.0 |
| Talc | Antistatic agent | 0.7 | 0.3 |
| Water | Solvent | qs | / |
| Isopropylic alcohol | Solvent | qs | / |

The dissolution rates of the thus obtained sustained-release granules were measured with the method described above:

The results are given in the following table 2:

| T (h) | % released (w/w) |
|---|---|
| 1 | 21.8% |
| 2 | 36.9% |
| 4 | 51.5% |
| 8 | 64.1% |
| 12 | 70.2% |

EXAMPLE 2

Step 1—Drug Loading 498 grams of neutral cores are placed in a coating-pan.

A 10% (w/w) binding solution of PVP K30, dissolved in isopropyl alcohol is prepared, then sprayed over neutral core as *Gingko biloba* extract is gradually added at the same time.

Granules are then sieved and dried for 10 hour at 60° C.

Step 2—Sustained-release Coating

A 10% (w/w) coating solution containing 14 grams of shellac in isopropyl alcohol is prepared and sprayed on the microgranules with spraying gun, alternatively with addition of an appropriate quantity of talc.

Coated microgranules are then sieved and dried in a coating pan at 65° C. for 10 hours.

The sustained-release microgranules resulting from the process have the following formula:

TABLE 3

| | Unit formula (g) | Percent formula |
|---|---|---|
| Ginkgo extract | 498.0 | 49.8% |
| Neutral granules | 418.0 | 41.8% |
| PVP K30 | 20.0 | 2% |
| Shellac | 14.0 | 1.4% |
| Talc | 50.0 | 5% |
| Isopropylic alcohol | Qs | a.q. |

The dissolution rates of total flavone glycosides from the sustained-release granules were measured according to the Chinese Pharmacopeia method:

The results are given in following

TABLE 4

| T (h) | % released (w/w) |
|---|---|
| 1 | 20.7% |
| 2 | 38.1% |
| 4 | 54.4% |
| 8 | 62.3% |
| 12 | 69.1% |

EXAMPLE 3

Sustained release microgranules comprising *Gingko biloba* are prepared according the process of example to example 2 (see table 5):

TABLE 5

| Name of ingredients | function | Unit formula (g) | Percentage formula (% w/w) |
|---|---|---|---|
| Ginkgo extract | Active substance | 120 | 49.8 |
| Neutral granules | Cores | 101 | 41.8 |
| PVP K30 | Binding agent | 4.82 | 2 |
| Shellac | Coating agent | 3.37 | 1.4 |
| Talc | Antistatic agent | 12.1 | 5 |
| Isopropylic alcohol | Solvent | qs | / |

Microgranules thus obtained are encapsulated in hard-gelatin capsules, each containing 120 mg of *Gingko biloba* extract, said capsules being packed in PVC/Alu blisters.

Stability of the resulting product was tested in long term conditions (25° C.±2° C./HR 60%±10%) and in accelerated conditions (40° C.±2° C./HR 75%±5%), as defined by ICH.

Results are summarized in tables 6 and 7.

Conclusion: After 3 months, results comply with specifications. The microgranules remain stable in both storage conditions.

*Ginkgo Biloba* Capsule120 mg—Accelerate Stability Study

TABLE 6

| | | | | | | | | |
|---|---|---|---|---|---|---|---|---|
| | | | Test results (40° C. ± 2° C./HR 75% ± 5%) | | | | | |
| Time | Water Content | | Ratio of Peak Area | Total Flavone Glycocides | Dissolution (%) | | | Terpene Lactone |
| (Month) | (%) | Appearance | quercetin/kae | content | 0.5 h | 2 h | 8 h | content |
| | <9.0 | Grey-yellow to dark brown spherical pellets | 0.8-1.5 | >>28.80 | <45 | <75 | >60 | / |
| 0 | 0.76 | Passed | 1.34 | 30.79 | 23.9 | 54.5 | 71.4 | 17.16 |
| 1 | 1.78 | Passed | 1.33 | 30.91 | 20.7 | 48.1 | 70.7 | 17.05 |
| 2 | 1.75 | Passed | 1.33 | 31.21 | 20.2 | 48.9 | 73.3 | 17.10 |
| 3 | 2.41 | Passed | 1.34 | 31.14 | 21.4 | 48.8 | 70.1 | 16.89 |

* specifications in bold characters

*Ginkgo Biloba* Capsule 120 mg—Long Term Stability Study

TABLE 7

| | | | | | | | | |
|---|---|---|---|---|---|---|---|---|
| | | | Test results (25° C. ± 2° C./HR 60% ± 10%) | | | | | |
| Time | Water Content | | Ratio of Peak Area of Flavonol | Total Flavone Glycocides content | Dissolution (%) | | | TerpeneLactone content |
| (Month) | (%) | Appearance | Aglucon | (mg/capsule) | 0.5 h | 2 h | 8 h | (mg/capsule) |
| | <9.0 | Grey-yellow to dark brown spherical pellets | 0.8-1.5 | >>28.80 | <45 | <75 | >60 | / |
| 0 | 0.76 | Passed | 1.34 | 30.79 | 23.9 | 54.5 | 71.4 | 17.16 |
| 1 | 1.21 | Passed | 1.35 | 31.16 | 26.4 | 54.7 | 70.9 | 17.10 |
| 2 | 1.75 | Passed | 1.34 | 31.88 | 26.0 | 55.4 | 79.2 | 17.04 |
| 3 | 1.94 | Passed | 1.34 | 31.40 | 26.0 | 55.3 | 75.0 | 17.00 |

* specifications in bold characters

The invention claimed is:

1. Sustained release microgranules containing a *Ginkgo biloba* extract, comprising:
   a neutral core coated with a layer, said layer containing *Ginkgo biloba* extract with at least one pharmaceutically acceptable excipient;
   an intermediate water-repellent layer, coating said core, comprising a thermoplastic excipient selected from the group consisting of partially hydrogenated oils, beeswax, carnauba wax, paraffin waxes, silicone waxes, C12-C18 fatty alcohols and fatty acids, solid, semi-synthetic glycerides, glycerol monoesters, diesters or triesters, polyoxyethylene glycols and glycosylated polyoxyethylenated glycerides, monostearate glycerides and mixtures thereof; and
   an outer polymeric layer which sustains the release of said extract from the active core;
   wherein the release of total flavone glycosides having the following profile of dissolution rates measured at 37.0° C.±0.5° C., with a Dissolution Test Apparatus I (Basket method at 100 rpm, 900 mL of purified water UV Detection: 272 nm):

| T (h) | DISSOLUTION (w/w) |
|---|---|
| 0.5 hour | ≦45% |
| 2 hours | <75% |
| 8 hours | >60%. |

2. Sustained release microgranules according to claim 1, wherein the profile is as follows:

| T (h) | Dissolution (w/w) |
|---|---|
| 0.5 hour | 5-45% |
| 2 hours | 30-70% |
| 8 hours | >60%. |

3. Sustained release microgranules according to claim 1, wherein the neutral core consists of a substance chosen from sugar, starch, mannitol, sorbitol, xylitol, cellulose, talc and mixtures thereof.

4. Sustained release microgranules according to claim 3, wherein the neutral core consists of a starch/sucrose core in 80/20 mass ratios.

5. Sustained release microgranules according to claim 1, wherein the *Ginkgo biloba* extract contains up to 40% by weight of flavonoids, and up to 10% by weight of terpenes.

6. Sustained release microgranules according to claim 5, wherein the *Ginkgo biloba* extract preferably contains up to 24% by weight of flavonoids, and up to 6% by weight of terpenes.

7. Sustained release microgranules according to claim 1, wherein the layer containing the *Ginkgo biloba* extract contains at least one pharmaceutically acceptable excipient, selected from the group comprising a binder, an antistatic agent or a lubricant.

8. Sustained release microgranules according to claim 7, wherein the binder is selected from the group consisting of cellulosic polymers, acrylic polymers, polyacrylate, povidones, copovidones, polyvinylalcohols, shellac, alginic acid, sodium alginate, starch, pregelatinized starch, sucrose and its derivatives, guar gum, polyethylene glycol.

9. Sustained release microgranules according to claim 8, wherein the binder is used in proportions of at most about 50% by weight of *Ginkgo biloba* extract.

10. Sustained release microgranules according to claim 7, wherein the antistatic agent, which can be used as flow aid, is selected from the group consisting of micronised or non micronised talc, fumed silica, colloidal silica, precipitated silica and mixtures thereof.

11. Sustained release microgranules according to claim 10, wherein the antistatic agent is used in proportions of at most 5% by weight relative to the weight of said granules of *Ginkgo biloba*.

12. Sustained release microgranules according to claim 7, wherein the lubricant is selected from the group consisting of magnesium stearate, stearic acid, sodium stearyl fumarate, micronised polyoxyethyleneglycol, leukine, sodium benzoate and mixtures thereof.

13. Sustained release microgranules according to claim 1, wherein the outer polymeric layer contains at least one coating agent selected from the group consisting of cellulosic polymers, acrylic polymers, shellac and mixtures thereof.

14. Sustained release microgranules according to claim 13, wherein the cellulosic polymer is selected among ethylcellulose, hydroxypropylcellulose and/or hydroxypropylmethylcellulose.

15. Sustained release microgranules according to claim 13, wherein the acrylic polymer is selected from insoluble acrylate ammonio-methacrylate copolymer, polyacrylate, or methacrylic copolymers, and combinations thereof.

16. Sustained release microgranules according to claim 13, wherein the outer polymeric layer additionally contains a plasticizer, a surfactant, an antistatic agent and/or a lubricant.

17. Sustained release microgranules according to claim 16, wherein the plasticizer is selected in the group consisting of dibutyl sebacate, triacetine, triethylacetate, triethylcitrate, ethylphtalate, or mixtures thereof.

18. Sustained release microgranules according to claim 17, wherein the plasticizer is used in proportions of at most about 30% by weight of the coating agents.

19. Sustained release microgranules according to claim 16, wherein the antistatic agent is selected from the group comprising micronised or non micronised talc, fumed silica, colloidal silica, precipitated silica and mixtures thereof.

20. Sustained release microgranules according to claim 16, wherein the antistatic agent is used in proportions of at most about 10%, by weight.

21. Sustained release microgranules according to claim 20, wherein the thermoplastic excipient comprised in the water-repellent layer is monostearate glyceride.

22. Process for the preparation of sustained release microgranules according to claim 1, comprising the successive steps consisting of:
   applying over a neutral core, a layer comprising *Gingko Biloba* extract, and at least one pharmaceutical excipient;
   coating said core with an intermediate layer over the thus obtained granules by spraying thereon a suspension, or a solution comprising a thermoplastic excipient
   coating the thus coated granules with an outer polymeric layer by spraying a suspension, a dispersion or a solution of a sustained-release coating composition,
   drying the thus obtained coated granules.

23. Process for the preparation of sustained release microgranules according to claim 22, wherein the layer is applied over the neutral cores by spraying a coating alcoholic solution containing the *Gingko Biloba* extracts and the excipient.

24. Process for the preparation of sustained release microgranules according to claim 23, wherein the alcoholic or aqueous alcoholic solution contains isopropylic alcohol.

25. Process for the preparation of sustained release microgranules according to claim 23, wherein the layer applied over the neutral cores is a 10% w/w binding solution of shellac dissolved in isopropyl alcohol.

26. Process for the preparation of sustained release microgranules according to claim 22, wherein the outer coating layer is a water dispersion of ethylcellulose at 16% w/w containing 25% w/w of dibutyl sebacate versus dry polymer.

27. Process for the preparation of sustained release microgranules according to claim 2, comprising the successive steps consisting of:
- applying over a neutral core, a layer comprising *Gingko Biloba* extract, and at least one pharmaceutical excipient;
- coating said core with an intermediate layer over the thus obtained granules by spraying thereon a suspension, or a solution comprising a thermoplastic excipient
- coating the thus coated granules with an outer polymeric layer by spraying a suspension, a dispersion or a solution of a sustained-release coating composition,
- drying the thus obtained coated granules.

* * * * *